(12) United States Patent
North et al.

(10) Patent No.: US 7,142,923 B2
(45) Date of Patent: Nov. 28, 2006

(54) IMPLANTABLE NEUROSTIMULATOR PROGRAMMING WITH BATTERY LONGEVITY INDICATION

(75) Inventors: Richard B. North, Baltimore, MD (US); Jeffrey M. Sieracki, Silver Spring, MD (US); David D. Brigham, Columbia, MD (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 10/696,501

(22) Filed: Oct. 29, 2003

(65) Prior Publication Data

US 2005/0177206 A1 Aug. 11, 2005

Related U.S. Application Data

(60) Provisional application No. 60/503,207, filed on Sep. 15, 2003, provisional application No. 60/448,457, filed on Feb. 21, 2003.

(51) Int. Cl.
*A61N 1/37* (2006.01)
(52) U.S. Cl. .............................. 607/30; 607/29; 607/46
(58) Field of Classification Search ............ 607/29–32, 607/59–60, 46
See application file for complete search history.

(56) References Cited

U.S. PATENT DOCUMENTS

| 4,026,305 | A | 5/1977 | Brownlee et al. |
| 4,041,955 | A | 8/1977 | Kelly et al. |
| 4,071,032 | A | 1/1978 | Schulman |
| 4,082,097 | A | 4/1978 | Mann et al. |
| 4,142,533 | A | 3/1979 | Brownlee et al. |
| 4,313,079 | A | 1/1982 | Lee |
| 4,373,527 | A | 2/1983 | Fischell |
| 4,390,020 | A | 6/1983 | Herpers |
| 4,448,197 | A | 5/1984 | Nappholz et al. |
| 4,542,532 | A | 9/1985 | McQuilkin |
| 4,550,370 | A | 10/1985 | Baker |
| 4,556,061 | A | 12/1985 | Barreras et al. |

(Continued)

FOREIGN PATENT DOCUMENTS

WO    WO 91/10471    7/1991

(Continued)

OTHER PUBLICATIONS

Fowler, K.R., "Neurological Stimulation System", Proceedings AAMI 21st Annual Meeting, Apr. 12-16, p. 27, 1986.

(Continued)

*Primary Examiner*—Robert E. Pezzuto
*Assistant Examiner*—Jessica L. Reidel
(74) *Attorney, Agent, or Firm*—Shumaker & Sieffert, P.A.

(57) ABSTRACT

A programming device used to program an implantable neurostimulator (INS) presents battery longevity information to a user to assist the user in selecting a program for the INS. The programming device directs the INS to deliver neurostimulation therapy according to a plurality of programs during a programming session. Each of the programs includes parameters that define the neurostimulation delivered according to that program. For example, each program may include as parameters a voltage or current pulse amplitude, a pulse width, a pulse rate, and a duty cycle. The program may also identify as parameters the electrodes selected from a set coupled to the INS and their polarities, e.g., anode or cathode, for delivery of neurostimulation according to that program. The programming device estimates battery drain rates for each of the programs tested during the programming session based on the parameters for that program, and presents battery longevity information to a user based on the estimated battery drain rates.

58 Claims, 6 Drawing Sheets

U.S. PATENT DOCUMENTS

| | | | |
|---|---|---|---|
| 5,080,096 | A | 1/1992 | Hooper et al. |
| 5,107,833 | A | 4/1992 | Barsness |
| 5,117,825 | A | 6/1992 | Grevious |
| 5,127,404 | A | 7/1992 | Wyborny et al. |
| 5,168,871 | A | 12/1992 | Grevious |
| 5,292,343 | A | 3/1994 | Blanchette et al. |
| 5,314,450 | A | 5/1994 | Thompson |
| 5,324,315 | A | 6/1994 | Grevious |
| 5,335,657 | A | 8/1994 | Terry, Jr. et al. |
| 5,344,431 | A | 9/1994 | Merritt et al. |
| 5,350,411 | A | 9/1994 | Ryan et al. |
| 5,354,319 | A | 10/1994 | Wyborny et al. |
| 5,369,364 | A | 11/1994 | Renirie et al. |
| 5,370,668 | A | 12/1994 | Shelton et al. |
| 5,383,909 | A | 1/1995 | Keimel |
| 5,391,193 | A | 2/1995 | Thompson |
| 5,402,070 | A | 3/1995 | Shelton et al. |
| 5,402,794 | A | 4/1995 | Wahlstrand et al. |
| 5,458,624 | A | 10/1995 | Renirie et al. |
| 5,591,217 | A | 1/1997 | Barreras |
| 5,620,474 | A | 4/1997 | Koopman |
| 5,693,076 | A | 12/1997 | Kaemmerer |
| 5,741,307 | A | 4/1998 | Kroll |
| 5,744,931 | A | 4/1998 | Arai et al. |
| 5,752,976 | A | 5/1998 | Duffin et al. |
| 5,766,232 | A | 6/1998 | Grevious et al. |
| 5,769,873 | A | 6/1998 | Zadeh |
| 5,769,877 | A | 6/1998 | Barreras, Sr. |
| 5,807,397 | A | 9/1998 | Barreras |
| 5,861,019 | A | 1/1999 | Sun et al. |
| 5,904,708 | A | 5/1999 | Goedeke |
| 5,938,690 | A | 8/1999 | Law et al. |
| 6,016,448 | A | 1/2000 | Busacker et al. |
| 6,108,579 | A | 8/2000 | Snell et al. |
| 6,148,235 | A | 11/2000 | Kuiper |
| 6,154,675 | A | 11/2000 | Juran et al. |
| 6,166,518 | A | 12/2000 | Echarri et al. |
| 6,167,309 | A | 12/2000 | Lyden |
| 6,185,461 | B1 | 2/2001 | Er |
| 6,308,102 | B1 | 10/2001 | Sieracki et al. |
| 6,400,988 | B1 | 6/2002 | Gurewitsch |
| 6,490,484 | B1 | 12/2002 | Dooley et al. |
| 6,584,355 | B1 | 6/2003 | Stessman |
| 6,609,032 | B1 | 8/2003 | Woods et al. |
| 6,659,968 | B1 | 12/2003 | McClure |
| 2002/0099416 | A1 | 7/2002 | Dooley et al. |
| 2002/0161328 | A1 | 10/2002 | Rogers |
| 2003/0065366 | A1 | 4/2003 | Merritt et al. |
| 2003/0093134 | A1* | 5/2003 | Bradley ............. 607/72 |
| 2003/0171789 | A1* | 9/2003 | Malek et al. ............. 607/60 |

FOREIGN PATENT DOCUMENTS

| | | |
|---|---|---|
| WO | WO 96/20754 | 7/1996 |
| WO | WO 00/24459 | 5/2000 |
| WO | WO 01/08749 | 2/2001 |
| WO | WO 02/49718 | 6/2002 |
| WO | WO 02/074368 | 9/2002 |

OTHER PUBLICATIONS

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological simulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochirurgica, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Advances in Neurology, vol. 63, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., "Consensus conference on the neurosurgical management of pain," Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation For Chronic Pain," Neurosurgery Clinics of North America, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu, L., Piantadosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, 2003.

Khalessi, A. A., Taylor, R. S., Brigham, D. D., North, R. B., "Automated, patient-interactive spinal cord stimulator adjustment: A cost-minimization analysis," Neurosurgery, 53:501-502, 2003.

U.S. Appl. No. 10/696,781, entitled "Neurostimulation Therapy Manipulation", filed Oct. 29, 2003, Richard A. North, Jeffrey M. Sieracki.

U.S. Appl. No. 10/696,494, entitled "Distributed System for Neurostimulation Therapy Programming", filed Oct. 29, 2003, Richard B. North, Kim R. Fowler, Jeffrey M. Sieracki.

U.S. Appl. No. 10/696,725, entitled "Failsafe Programming of Implantable Medical Devices", filed Oct. 29, 2003, Richard B. North, Jeffrey M. Sieracki.

U.S. Appl. No. 10/696,491, entitled "Body Region Indication", filed Oct. 29, 2003, Richard B. North, Jeffrey M. Sieracki.

U.S. Appl. No. 10/696,778, entitled "Applying Filter Information to Identify Combinations of Electrodes", filed Oct. 29, 2003, Richard B. North, Jeffrey M. Sieracki.

* cited by examiner

IMPLANTABLE NEUROSTIMULATOR PROGRAMMING WITH BATTERY LONGEVITY INDICATION

This application claims priority from U.S. Provisional Application Ser. No. 60/448,457, filed Feb. 21, 2003, and U.S. Provisional Application Ser. No. 60/503,207, filed Sep. 15, 2003. The entire content of both Provisional Applications is incorporated herein by reference.

TECHNICAL FIELD

The invention relates to implantable neurostimulators, and more particularly to programming of implantable neurostimulators.

BACKGROUND

Implantable neurostimulators are used to deliver neurostimulation therapy to patients to treat a variety of symptoms or conditions such as chronic pain, tremor, Parkinson's disease, epilepsy, incontinence, or gastroparesis. Typically, implantable neurostimulators deliver neurostimulation therapy in the form of electrical pulses via leads that include electrodes. To treat the above-identified symptoms or conditions, for example, the electrodes may be located proximate to the spinal cord, pelvic nerves, or stomach, or within the brain of a patient.

A clinician may select values for a number of programmable parameters in order to define the neurostimulation therapy to be delivered to a patient. For example, the clinician may select a voltage or current amplitude and pulse width for a stimulation waveform to be delivered to the patient, as well as a rate at which the pulses are to be delivered to the patient and a duty cycle. The clinician may also select as parameters particular electrodes within the electrode set carried by the leads to be used to deliver the pulses, and the polarities of the selected electrodes. A group of parameter values may be referred to as a program in the sense that they drive the neurostimulation therapy to be delivered to the patient.

Typically, a clinician selects parameter values for a number of programs to be tested on a patient during a programming session using a programming device. The programming device directs the implantable neurostimulator implanted in the patent to deliver neurostimulation according to each program, and the clinician collects feedback from the patient, e.g., rating information, for each program tested on the patient. The clinician then selects one or more programs for long-term use by the implantable neurostimulator based on the rating information. Some programming devices automatically present programs defined by the clinician to the INS, and collect feedback from the patient. One such programming device is described in U.S. Pat. No. 6,308,102, issued to Sieracki et al., which is incorporated herein by reference in its entirety.

Implantable neurostimulators typically include a nonrechargeable battery that provides power for delivery of neurostimulation. The longevity of the battery depends on the parameters of the program selected by the clinician for long-term delivery of neurostimulation. In particular, the battery longevity is inversely proportional to the pulse amplitude, pulse rate, pulse width, and duty cycle specified by the program, and to the load presented to the battery. Generally speaking, the load presented to the battery depends on the number of electrodes specified by the program for delivery of neurostimulation.

When the battery of an implantable neurostimulator is depleted, the implantable neurostimulator must be explanted from the patient and replaced. Replacement of an implantable neurostimulator is costly, and because it requires a surgical procedure the patient incurs risks associated with surgery. Nonetheless, clinicians typically do not consider battery longevity, e.g., the amount of time an implantable neurostimulator will be able to deliver neurostimulation according to a program before its battery expires, when selecting programs from among those tested during a programming session. This is despite the fact that battery longevities can vary greatly among the programs tested, e.g., from on the order of months up to two or more years.

SUMMARY

In general, the invention is directed toward techniques for presenting battery longevity information to a user during a programming session for programming an implantable neurostimulator (INS). A programming device directs the INS to deliver neurostimulation therapy according to a plurality of programs during the programming session. The programming device estimates a battery drain rate for each of the tested programs. In some embodiments, the programming device estimates a battery longevity for each of the tested programs based on the estimated drain rate, e.g., estimates a length of time that the INS will be able to deliver neurostimulation according to the program before the INS must be explanted and replaced due to battery depletion.

Each of the programs includes parameters that define the neurostimulation delivered according to that program. For example, each program may include as parameters a voltage or current pulse amplitude, a pulse width, a pulse rate, and a duty cycle. The program may also identify as parameters the electrodes selected from a set coupled to the INS and their polarities, e.g., anode or cathode, for delivery of neurostimulation according to that program. The programming device estimates battery drain rates for each of the programs tested during the programming session based on the parameters for that program.

In particular, the programming device estimates the battery drain for a program based on the program parameters that define the neurostimulation waveform, and an estimate of the load presented to the battery during delivery of the neurostimulation waveform. In some embodiments, the programming device estimates the load based on the number of anodes and cathodes for the program, and an assumed per-electrode impedance. In some embodiments, the programming device alternatively or additionally estimates the load based on device configuration information, such as an INS type, lead type, and/or electrode locations. The programming device may receive the device configuration information from the user, and identify components of the total load presented to the battery from look-up tables based on the received device configuration information. In other embodiments, the programming device may direct the INS to measure the impedance presented by each electrode coupled thereto, receive the measured impedance values, and determine the load for a particular program based on the impedances for the anodes and cathodes selected for that program.

In some embodiments, the estimated battery drain rates are presented to the user within a listing of the programs. In other embodiments, a listing of battery longevities is presented instead of or in addition to the drain rates. The programming device may estimate battery longevities based on the estimated drain rates and the capacity of the battery, which may be determined from a look-up table based on device type information received from the user. Alternatively, the programming device may calculate battery longevities given the estimated drain rates, the capacity of the battery and one or more equations that determine battery longevity. The battery longevities may be presented to the user as, for example, an estimated number of years or months until explant. The listing may be ordered according to the battery drain rates and/or battery longevities to allow a user to select a program that provides a low drain rate and high longevity.

In some embodiments, the programming device additionally receives rating information for each of the programs tested during the programming session. The rating information may include, for example, an effectiveness score and/or an estimation of the overlap of a pain area of the patient with a paresthesia area resulting from delivery of neurostimulation according to the program. In exemplary embodiments, the rating information is presented alongside the battery drain rates and/or longevities within the list, and the user may select to order the list according to either the rating information or the battery longevity information.

In one embodiment, the invention is directed to a method in which an implantable neurostimulator is directed to deliver neurostimulation according to a plurality of programs during a programming session, each of the programs including a plurality of parameters that define delivery of neurostimulation according to that program. A battery drain rate is estimated for each of the programs based on the parameters for that program, and battery longevity information is presented to a user based on the estimated battery drain rates.

In another embodiment, the invention is directed to a programming device that includes a telemetry circuit, a user interface, and a processor. The processor directs an implantable neurostimulator to deliver neurostimulation according to a plurality of programs during a programming session via the telemetry circuit, each of the programs including a plurality of parameters that define delivery of neurostimulation according to that program. The processor estimates a battery drain rate for each of the programs based on the parameters for that program, and presents battery longevity information to the user based on the estimated battery drain rates.

In another embodiment, the invention is directed to a computer-readable medium containing instructions. The instructions cause a programmable processor to direct an implantable neurostimulator to deliver neurostimulation according to a plurality of programs during a programming session, each of the programs including a plurality of parameters that define delivery of neurostimulation according to that program, estimate a battery drain rate for each of the programs based on the parameters for that program, and present battery longevity information to a user based on the estimated battery drain rates.

The invention may provide advantages. For example, by presenting battery longevity information, a programming device according to the invention may allow a clinician to select a program for long-term use from among programs tested that provides greater battery longevity than a program selected based on efficacy alone. Battery longevity may vary widely among tested programs that provide similar efficacy. Consequently, a programming device according to the invention may allow a clinician to identify a program that strikes a desirable balance between battery longevity and efficacy. By presenting the battery drain rates and/or longevities and the rating information in a single sortable list, the programming device may allow the clinician to more easily identify such a program. Further, by allowing the clinician to select a program that provides a greater battery longevity than a program selected based on efficacy alone, the programming device may allow explanation and replacement of an implantable neurostimulator to be delayed relative to the time at which they would have occurred if a program had been selected without regard to battery longevity.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
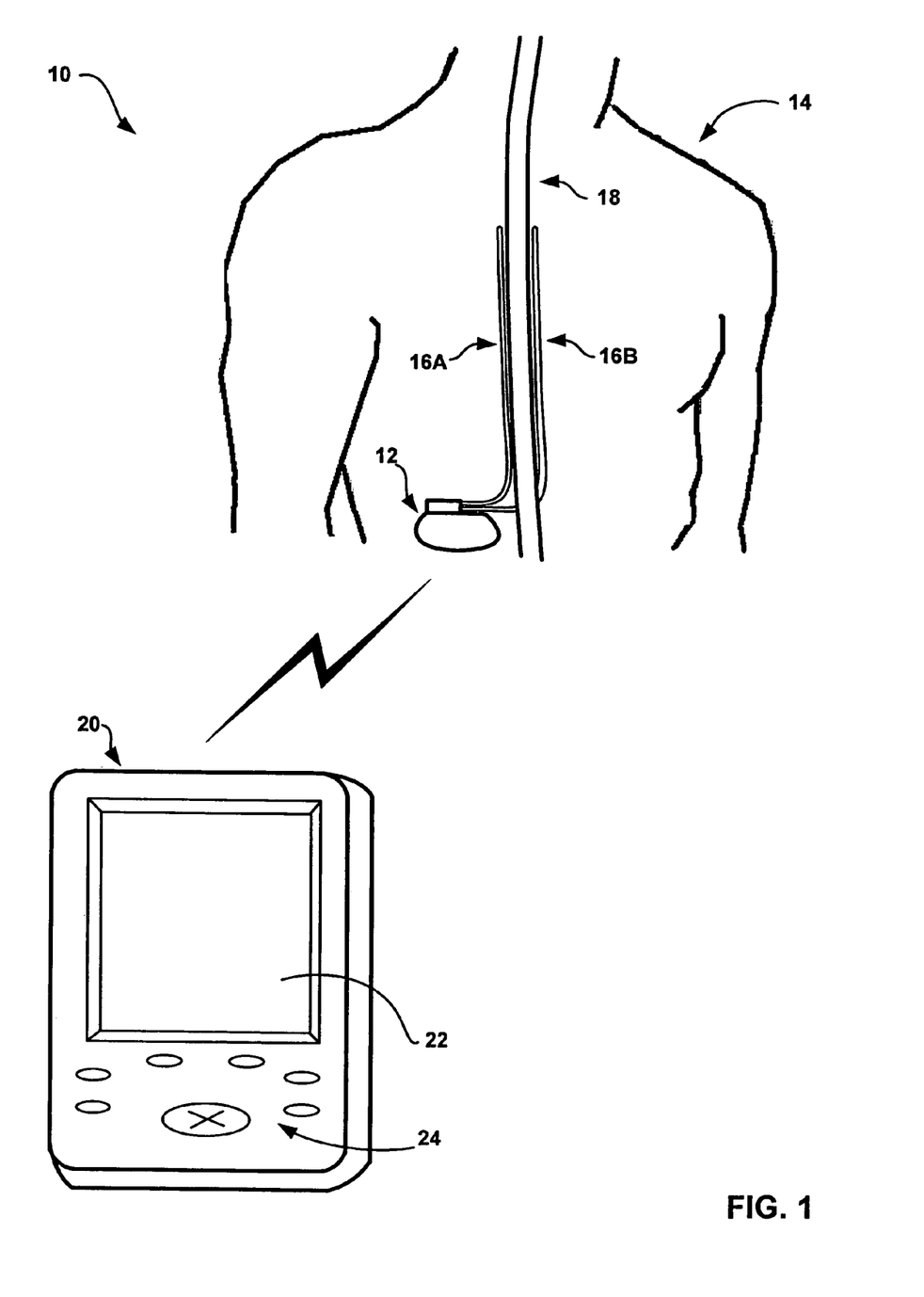
FIG. 1 is a conceptual diagram illustrating an exemplary environment in which battery longevity information is presented to a user during a programming session according to the invention.

FIG. 1 is a conceptual diagram illustrating an exemplary environment 10 in which battery longevity information is presented to a user during a programming session according to the invention. Environment 10 includes an implantable neurostimulator (INS) 12, which is shown in FIG. 1 implanted within a patient 14. INS 12 delivers neurostimulation therapy to patient 14 via leads 16A and 16B (hereinafter "leads 16").

In the illustrated configuration, leads 16 are implanted proximate to the spinal cord 18 of patient 14, and INS 12 delivers spinal cord stimulation (SCS) therapy to patient 14 in order to, for example, reduce pain experienced by patient 14. Leads 16 include electrodes (not shown in FIG. 1), and INS 12 delivers neurostimulation to spinal cord 18 via the electrodes. INS 12 may be an implantable pulse generator, and may deliver neurostimulation to spinal cord 18 in the form of electrical pulses.

INS 12 delivers neurostimulation according to a program. The program may include values for a number of parameters, and the parameter values define the neurostimulation therapy delivered according to that program. In embodiments where INS 12 delivers neurostimulation therapy in the form of electrical pulses, the parameters include voltage or current pulse amplitudes, pulse widths, pulse rates, duty cycles, and the like. Further, the parameters for a program include information identifying which electrodes have been selected for delivery of pulses according to the program, and the polarities of the selected electrodes, e.g., anode or cathode.

Environment 10 also includes a programming device 20. Programming device 20 may, as shown in FIG. 1 be a handheld computing device. Programming device 20 includes a display 22, such as a LCD or LED display, to display information to a user. Programming device 20 may also include a keypad 24, which may be used by a user to interact with programming device 20. In some embodiments, display 22 may be a touch screen display, and a user may interact with programming device 20 via display 22. A user may additionally or alternatively interact with clinician programmer 20 using peripheral pointing devices, such as a stylus or mouse. Keypad 24 may take the form of an alphanumeric keypad or a reduced set of keys associated with particular functions.

A clinician (not shown) may use programming device 20 to program neurostimulation therapy for patient 12. In some embodiments, the clinician specifies programs by selecting program parameter values, tests the specified programs on patient 12, and receives feedback, e.g., rating information, for each of the tested programs from the patient. The clinician enters the feedback into programming device 20.

In other embodiments, programming device 20 provides an automated or semi-automated programming routine in which programming device 20 automatically tests clinician specified programs or programs automatically generated by programming device 20 on patient 14. In such embodiments, either or both of the clinician and patient 14 may interact with programming device 20 during testing of the generated programs to, for example, enter rating information for each of the programs. An exemplary programming device that provides a semi-automated programming routine is described in U.S. Pat. No. 6,308,102, issued to Sieracki et al.

In either case, programming device 20 sends each of the programs to be tested to IMD 12 using radio-frequency (RF) telemetry techniques known in the art. For example, programming device 20 may send program parameters as commands, and may send other commands necessary to effect reprogramming of IMD 12 via device telemetry. IMD 12 receives and decodes the commands, and stores the program parameters in registers, or the like, for use in defining the neurostimulation delivered to patient 14 according to that program.

INS 12 includes a battery (not shown in FIG. 1) that provides power for delivery of neurostimulation energy and other functions performed by INS 12, e.g., processing, memory and telemetry functions. Delivery of neurostimulation energy, however, accounts for by far the most significant drain on the battery of INS 12. The drain on the battery of INS 12 caused by delivery of neurostimulation according to a program depends on the parameters of that program, e.g., the pulse amplitude, width and rate, duty cycle, and the combination of electrodes selected for delivery neurostimulation according to the program.

As will be described in greater detail below, programming device 20 estimates a battery drain rate for each of the programs tested based on the program parameters. In some embodiments, programming device 20 presents the estimated battery drain rates for programs tested during the programming session. In other embodiments, programming device 20 further estimates a battery longevity for each of the tested programs, e.g., estimates a length of time that INS 12 will be able to deliver neurostimulation according to the program before INS 12 must be explanted and replaced due to battery depletion. The estimated battery longevity may be based on the estimated battery drain rates. Programming device 20 may present the battery longevities to the clinician in addition to or instead of presenting the battery drain rates. By presenting one or both of the battery drain rates and longevities, programming device 20 allows the clinician to consider battery longevity when selecting one or more programs, and to select programs from among those tested that provide favorable drain rates and longevities. In this manner, the clinician may take into account not only the efficacy and side effects associated with a particular neurostimulation program, but also power consumption.

Figure 2:
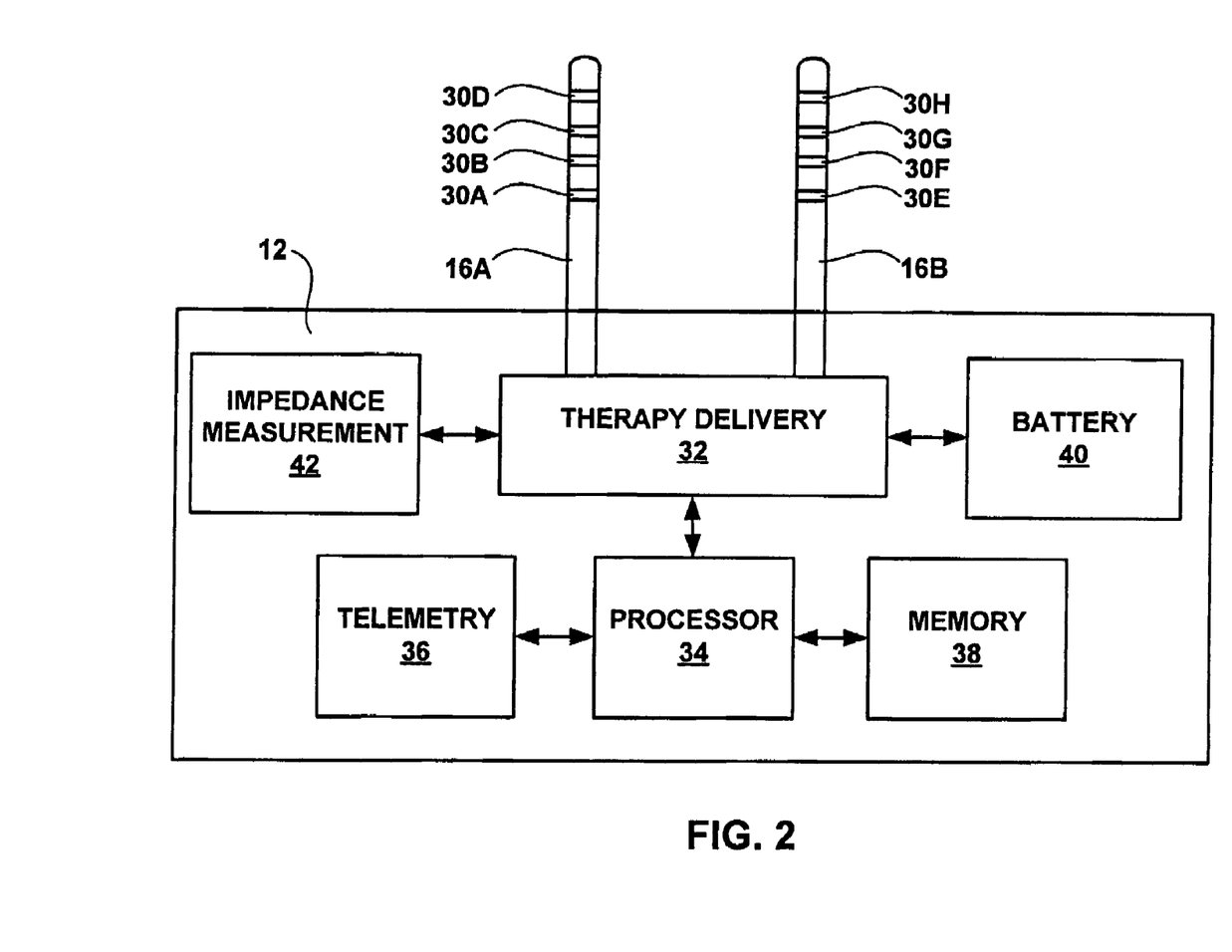
FIG. 2 is a block diagram illustrating an example implantable neurostimulator.

FIG. 2 is a block diagram illustrating an example configuration of INS 12. INS 12 may deliver neurostimulation therapy via electrodes 30A-D of lead 16A and electrodes 30E-H of lead 16B (collectively "electrodes 30"). Electrodes 30 may be ring electrodes. The configuration, type, and number of electrodes 30 illustrated in FIG. 2 are merely exemplary.

IMD 16 includes a therapy delivery circuit 32. Electrodes 30 are electrically coupled to therapy delivery circuit 32 via leads 16. Therapy delivery circuit 32 may, for example, include an output pulse generator. Therapy delivery circuit 32 delivers electrical pulses to patient 14 via at least some of electrodes 30 under the control of a processor 34.

Processor 34 controls therapy delivery circuit 32 to deliver stimulation according to program stored with a memory 38. Specifically, processor 34 controls therapy delivery circuit 32 to deliver electrical stimulation pulses with an amplitude, width, and rate specified by the program, and may activate therapy delivery circuit 32 to deliver stimulation pulses according to a duty cycle specified by the program. Processor 34 also controls circuit 32 to deliver the pulses via a selected subset of electrodes 30 with selected polarities, as specified by the program.

As described above, INS 12 may be reprogrammed a number of times during a programming session to test a number of programs. For each program tested, INS 12 receives a number of commands, including the program parameters, from programming device 20 via a telemetry circuit 36 that allow processor 34 to communicate with programming device 20 via wireless telemetry techniques known in the art. The program parameters are stored within a memory 38 as the program used by processor 34 to control delivery of neurostimulation. Processor 34 may include a microprocessor, a controller, a digital signal processor (DSP), an application specific integrated circuit (ASIC), a field-programmable gate array (FPGA), discrete logic circuitry, or the like. Memory 38 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

As shown in FIG. 2, INS 12 includes a battery 40. Battery 40 may be a non-rechargeable, e.g., primary, battery. Battery 40 may take the form of any of a variety of lithium-ion batteries well known in the implantable medical device arts. Battery 40 is illustrated in FIG. 2 as providing power to therapy delivery circuit 32 for generation of stimulation pulses. Although not illustrated in FIG. 2, battery 40 may provide power to each of components 32–38 of INS 12. However, as indicated above, delivery of energy necessary to support neurostimulation therapy by therapy delivery circuit 32 represents by far the most significant drain on battery 40.

In some embodiments, INS 12 may also, as shown, include an impedance measurement circuit 42 to measure the impedance at each of electrode 30. Impedance measurement circuit 42 may include any circuits and apply any techniques known in the implantable medical device arts for measuring impedances, such as measuring the change in voltage across a capacitor during delivery of a pulse, to determine the impedance for each of electrodes 30. Processor 34 may control impedance measurement circuit 42 to measure impedances for electrodes 30 upon receiving a command from programming device 20, and may provide the measured impedances to programming device 20 via telemetry circuit 36 for calculation of battery drain rates, as will be described in greater detail below with reference to FIG. 3

Figure 3:
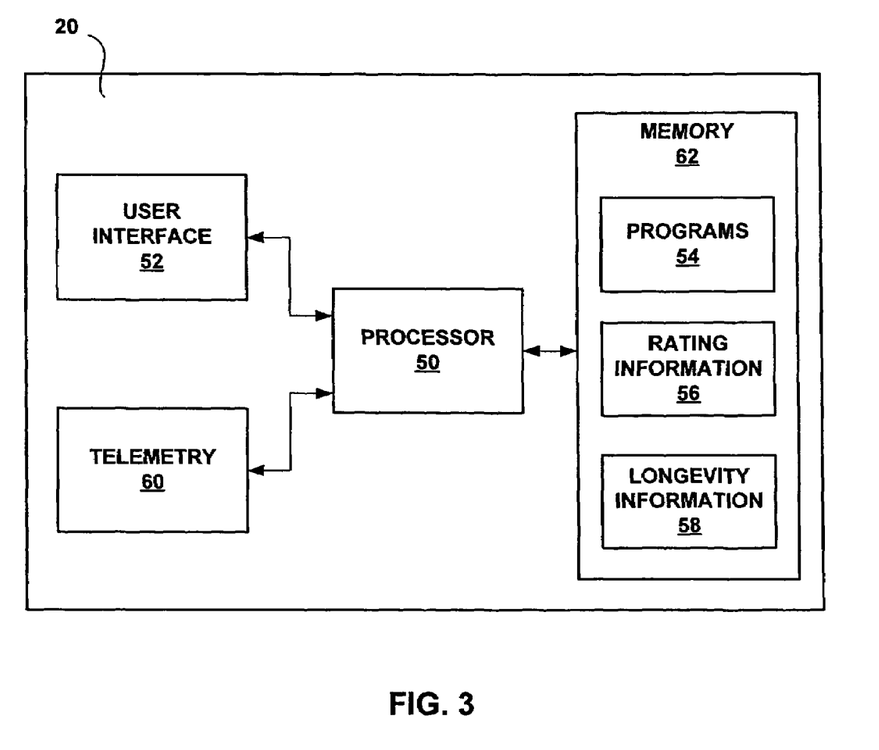
FIG. 3 is a block diagram illustrating an example programming device that presents battery longevity information during a programming session according to the invention.

FIG. 3 is a block diagram illustrating an example configuration of programming device 20. Programming device 20 includes a processor 50 and a user interface 52 that allows a user, such as the clinician or patient 14, to interact with processor 50. User interface 52 may include display 22 and keypad 24 (FIG. 1), and allow the clinician or patient 14 to, for example, specify parameters for a number of programs 54 to test during a programming session, provide rating information 56 for tested programs, and view rating information 56 and battery longevity information 58 for each of the tested programs.

Processor 50 provides programs 54 to INS 12 for testing via a telemetry circuit 60, which allows processor 50 to communicate with INS 12 according to wireless telemetry techniques known in the art. Processor 50 stores programs 54 specified by the clinician within a memory 62 of programming device 20. Rating information 56 and longevity information 58 for each of the programs is stored within memory 62 in association with the respective programs 54.

Rating information 56 may include, for example, numeric ratings of the efficacy of each of the programs. Rating information 56 may also include a pain map that indicates regions of pain within the body of patient 14, and paresthesia maps for each program that indicate regions of paresthesia resulting from delivery of neurostimulation according to that program. Rating information 56 may include numeric calculations of overlap between the pain map and the paresthesia map for each program. Processor 50 may receive rating information 56 from either or both of the clinician and patient 14. Exemplary techniques for collecting, calculating, and displaying such rating information are described in U.S. Pat. No. 6,308,102, issued to Sieracki et al.

Longevity information 58 may include either or both of estimated drain rates and estimated longevities of battery 40 for each of programs 54. Processor 50 estimates a drain rate for battery 40 for each of programs 54 using well-known techniques for calculating battery drain rate based on the pulse amplitude, width and rate of a stimulation waveform, and the load presented to battery 40 during delivery of the stimulation waveform. In some embodiments, processor 50 further estimates a longevity of battery 40 for each program based on a capacity of battery 40, the estimated drain rate for each program, and a duty cycle for each program. Processor 50 may estimate the longevities as a time to explant, e.g., expiration of battery 40, based on constant delivery of stimulation according to programs 54, or an estimation of the amount of time patient 14 will use INS 12 over the course of a day, week, month, year, or the like. Processor 50 may determine the capacity of battery 40 from a look-up table stored in memory 62 based on device type information received from the clinician.

Processor 50 may determine the load presented to battery 40 for each of programs 54 using a variety of techniques. In some embodiments, processor 50 estimates the load based on the number of anodes and cathodes specified for the program, and an assumed per-electrode impedance, which may be stored in memory 62. The assumed per-electrode impedance value may be an average of impedances measured experimentally or gleaned from clinical data, and may be, for example, 700–1000 Ohms. Processor 50 may calculate the estimated load using the formula for parallel loads:

$$1/R_{(TOTAL)} = 1/R_{(CATHODES)} + 1/R_{(ANODES)}$$

where $R_{(TOTAL)}$ is the estimated load and each of $R_{(CATHODES)}$ and $R_{(ANODES)}$ is equal to the assumed per-electrode impedance value.

In some embodiments, the processor 50 alternatively or additionally estimates the load based on device configuration information, such as an INS type, lead type, and/or electrode locations. Processor 50 may receive the device configuration information from the clinician via user interface 52, and may identify components of the total load presented to the battery from look-up tables stored in memory 62 based on the received device configuration information. In other embodiments, to achieve greater accuracy in the drain rate estimate, processor 50 may direct INS 12 to measure, rather than estimate, the impedance presented by each of electrodes 30 coupled thereto, and receive the measured impedance values via telemetry circuit 60. Processor 50 may then determine the load for a particular program based on the measured impedances for the anodes and cathodes selected for that program using the formula for parallel loads illustrated above. In exemplary embodiments, processor 50 directs INS 12 to measure impedances before testing of programs 54.

Processor 50 may include a microprocessor, a controller, a DSP, an ASIC, an FPGA, discrete logic circuitry, or the like. A memory 62 may include program instructions that, when executed by processor 50, cause programming device 20 to perform the functions ascribed to programming device 20 herein. Memory 62 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 4:
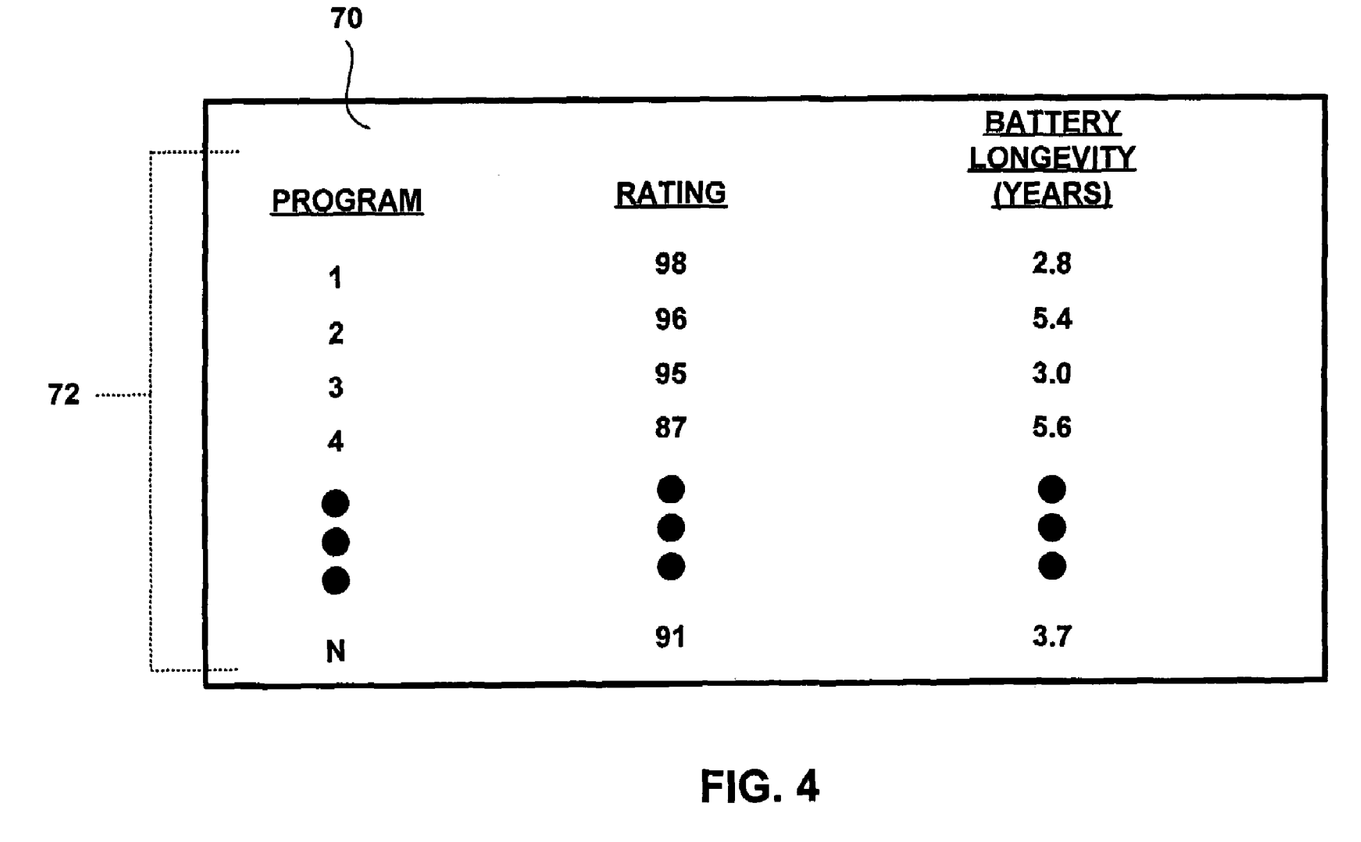
FIG. 4 is a conceptual diagram illustrating an example graphical user interface that the programming device of FIG. 3 may present to a user.

FIG. 4 is a diagram illustrating an example graphical user interface (GUI) 70 that programming device 20, and more particularly processor 50 of programming device 20, may present to the clinician via user interface 52, e.g., via display 22. In some embodiments, processor 50 presents the estimated battery drain rates to the clinician via user interface 52. In other embodiments, processor 50 presents battery longevities instead of or in addition to the drain rates via user interface 52. In exemplary embodiments, processor 50 presents the drain rates and/or longevities within a listing of programs 54 tested on patient 14, which may be ordered according to the battery drain rates and/or battery longevities to allow a user to select a program that provides a low drain rate and high longevity.

In the illustrated embodiment, processor 50 presents a list 72 of programs 54 tested on patient 14 that includes longevities estimated for each of the programs 54. As illustrated in FIG. 4, the battery longevities may be presented to the user as an estimated number of years until explant. Processor 50 also presents rating information 56, which in this case is a numeric efficacy rating, for each program to the clinician within list 72. In exemplary embodiments, the clinician may order list 72 based on either or both of rating and longevity, to more easily compare programs and to, for example, select a program that provides better longevity from among those with similar ratings.

Each item in list 72 may be selected by the clinician to obtain additional information. For example, the clinician may click on program "1" to determine the details associated with program 1, such as the electrode configuration, amplitude, frequency, and pulse width. In this manner, the clinician can readily assess not only the drain rate, battery longevity and rating associated with each program, but also the underlying details of the program itself.

Figure 5:
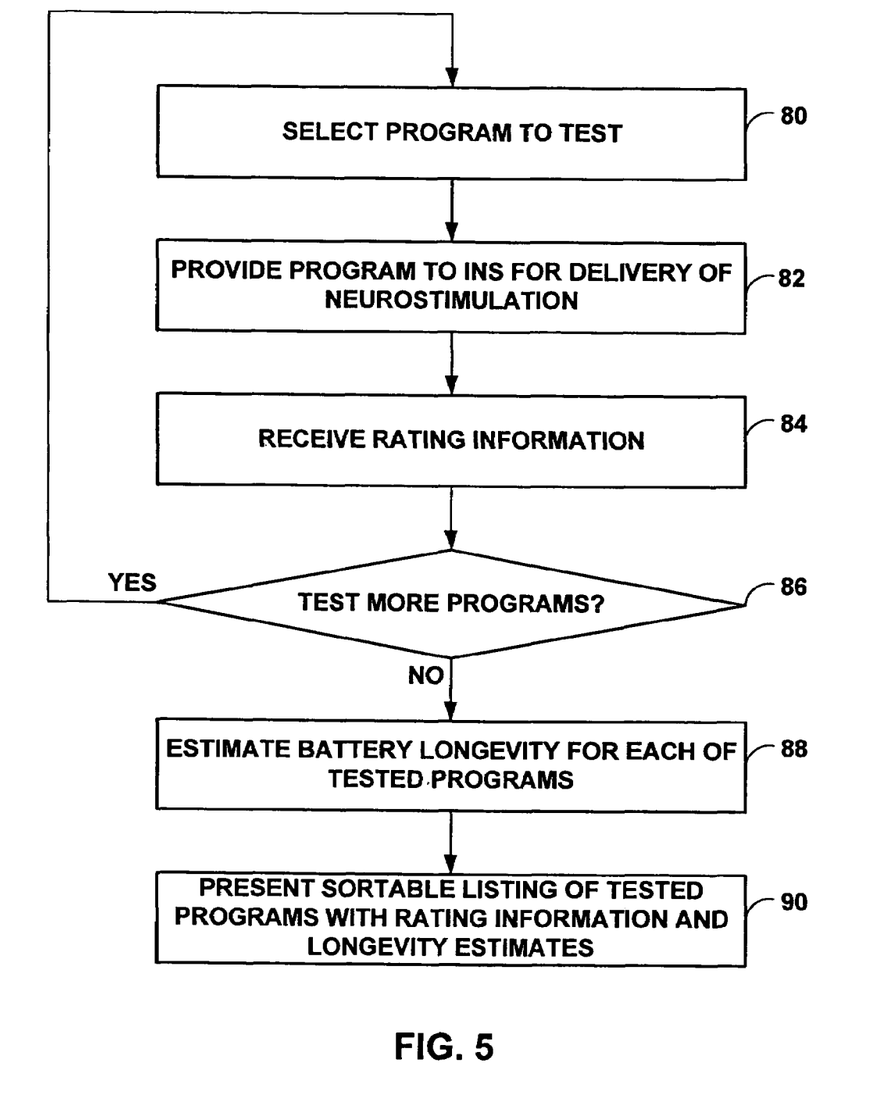
FIG. 5 is a flow diagram illustrating an example operation of the programming device of FIG. 3 to present battery longevity information to a user during a programming session.

FIG. 5 is a flow chart illustrating an example operation of programming device 20 to present battery longevity information 58 to a user during a programming session. Processor 50 selects a program 54 to test on patient 14 from among programs 54 specified by the clinician (80), and provides the program to INS 12 via telemetry circuit 60 so that INS 12 may deliver neurostimulation to patient 14 according to the selected program (82). Processor 50 may select the program 54 based on input received from the clinician via user interface 52, or automatically from a listing of specified programs 54. Processor 50 receives rating information 56 for the program from one or both of the clinician and patient 14 via user interface 52, and stores the rating information 56 within memory 62 in association with the program 54 (84).

Processor 50 continues to select programs 54 to test until either no more specified programs 54 remain to be tested or the clinician indicates that testing of programs is complete (86). When testing of programs 54 is complete, processor 50 estimates battery longevities for each of the tested programs, and stores the longevities as longevity information 58 in association with the respective programs 54 (88). Processor 50 estimates a drain rate for each of the programs, and estimates the longevities from the drain rates, as described above. Further, processor 50 may estimate drain rates and longevities according to any of the techniques described above. Processor 50 presents a sortable list 72 of tested programs 54, and associated rating information 56 and estimated longevities 58 to the clinician via user interface 52 (90).

Processor 50 may estimate drain rates and/or longevities at any time prior to, during, or following testing of programs 54. However, estimation of drain rates and/or longevities after testing of programs may allow changes made to the parameters of the programs 54 during testing, e.g., manipulation of amplitude, to be considered. Further, as indicated above, processor 50 need not estimate or display longevities. Rather processor 50 may simply display the estimated drain rates to the clinician.

Figure 6:
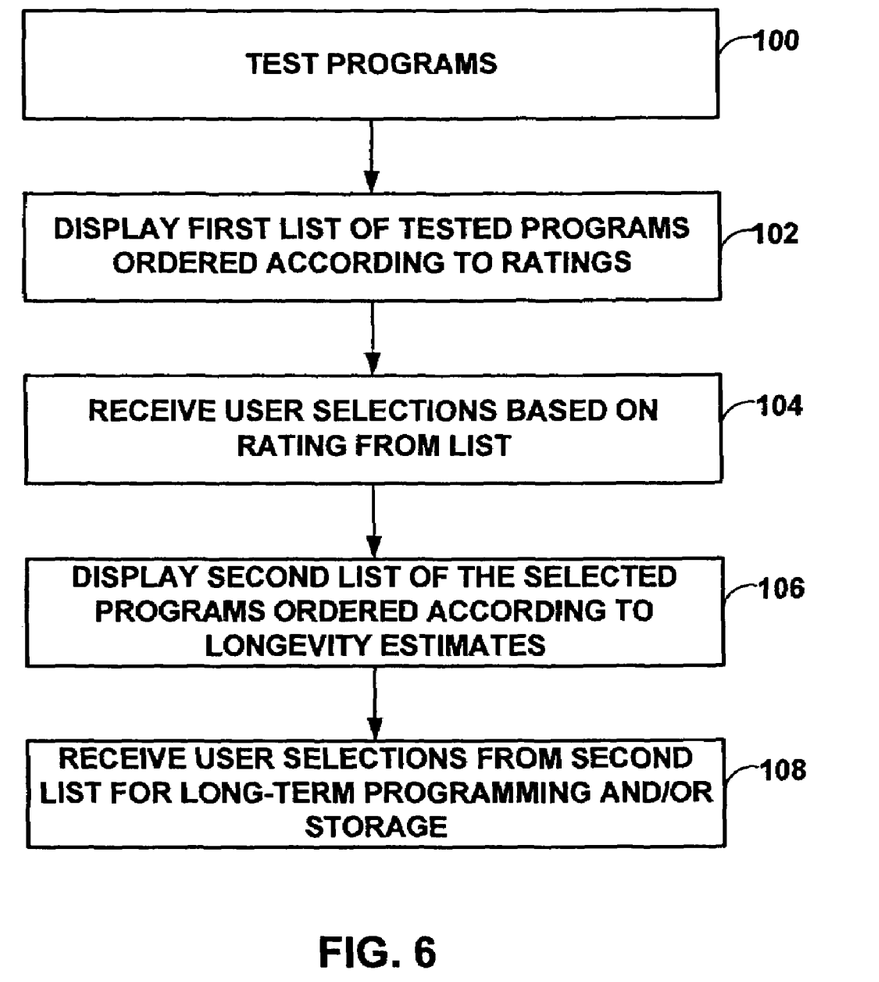
FIG. 6 is a flow diagram illustrating another example operation of the programming device of FIG. 3 during a programming session.

FIG. 6 is a flow diagram illustrating another example operation of programming device 20 during a programming session. Specifically, FIG. 6 illustrates operation of programming device 20 to present longevity information 58 for a subset of tested programs 54 that provide acceptable stimulation. Operation of programming device 20 in this manner allows a user, such as a clinician, to first identify a subset of acceptable programs 54 from among those tested based on rating information 56, and then select programs for long-term use from the subset based on longevity. Sequential presentation of rating information 56 and longevity information 58 may allow the user to more easily identify programs that are both efficacious and provide desirable longevity, while allowing programming device 20 to only estimate battery drains, and in some cases longevities, for a subset of the programs tested during the programming session.

During the programming session for IMD 12, programming device 20 tests programs 54 by directing IMD 12 to deliver neurostimulation to patient 14 according to programs 54(100). Programming device 20 collects rating information 56 relating to the efficacy of programs 54 from at least one of the clinician and patient 14 during testing of programs 54, as described above. After programs 54 have been tested, programming device 20 displays a list of the tested programs 54 ordered according to rating information 56 (102), and receives selections made by a user, such as the clinician, from the list (104).

Programming device 20 estimates drain rates and in some embodiments longevities, i.e., longevity information 58, for the selected programs, and displays a list of the selected programs ordered according the longevity information 58 (106). Programming device 20 receives one or more selections made by the clinician from the list, and provides the selected programs to IMD 12 via device telemetry for long-term use in delivery of neurostimulation therapy to patient 14 (108). In some embodiments, programming device 20 may also store highly rated programs with desirable longevities from the subset list within memory 62, or some other memory, such as a memory accessed via a network, for later selection by the clinician or patient 14 during a follow-up visit.

Various embodiments of the invention have been described. However, those skilled in the art will appreciate that various modifications may be made to the described embodiments without departing from the scope of the invention. For example, although estimation of drain rates and battery longevities, and presentation of such battery longevity information has been described herein as being performed by a single programming device, the invention is not so limited. Rather, such functions may be performed by two or more computing devices, which may communicate via a wired or wireless connection, or via a network. These and other embodiments are within the scope of the following claims.

The invention claimed is:

1. A method comprising:
   directing an implantable neurostimulator to deliver neurostimulation according to a plurality of programs during a programming session, each of the programs including a plurality of parameters that define delivery of neurostimulation according to that program;
   estimating a battery drain rate for each of the programs based on the parameters for that program; and
   presenting battery longevity information for each of the programs to a user based on the battery drain rates.

2. The method of claim 1, wherein the parameters for each of the programs include at least one of a pulse amplitude, a pulse width, a pulse rate, and a duty cycle.

3. The method of claim 1, wherein the parameters for each of the programs include a number of anodes and a number of cathodes for delivery of neurostimulation according to that program, and estimating a battery drain rate for one of the programs comprises:
   estimating a load for the program based on the number of anodes and the number of cathodes; and
   estimating the battery drain rate based on the estimated load.

4. The method of claim 3, wherein estimating a load comprises estimating the load based on an assumed per-electrode impedance.

5. The method of claim 1, wherein estimating a battery drain rate for one of the programs comprises:
   receiving device configuration information;

estimating a load for the program based on the device configuration information; and estimating the battery drain rate based on the estimated load.

6. The method of claim 5, wherein the device configuration information includes at least one of an implantable neurostimulator type, a lead type, and electrode locations.

7. The method of claim 1, wherein the parameters for each of the programs include an identification of anodes and cathodes for delivery of neurostimulation according to that program, and estimating a battery drain rate for one of the programs comprises:

measuring an impedance for each of the anodes and cathodes identified by the program;

calculating a load based on the measured impedances; and estimating the battery drain rate based on the load.

8. The method of claim 1, wherein presenting battery longevity information for each of the programs to a user comprises presenting the battery longevity information within a list of the programs.

9. The method of claim 8, further comprising ordering the list according to the battery longevity information.

10. The method of claim 8, further comprising:

receiving rating information for each of the programs; and presenting the rating information within the list.

11. The method of claim 10, further comprising ordering the list according to at least one of the battery longevity information and the rating information.

12. The method of claim 10, wherein the rating information for each of the programs includes at least one of an efficacy score and an estimation of overlap of pain and paresthesia.

13. The method of claim 1, further comprising:

receiving rating information for each of the programs;

presenting a first list of the tested programs, the first list including the rating information and ordered according to the rating information;

receiving selections made by the user from the first list;

presenting a second list that includes the programs selected from the first list and the longevity information associated with the selected programs, the second list ordered according to the longevity information;

receiving a selection made by the user of at least one program from the second list; and programming the implantable neurostimulator with the selected program.

14. The method of claim 13, wherein estimating a battery drain rate for each of the programs comprises estimating the drain rate for each of the programs selected from the first list upon selection from the first list.

15. The method of claim 13, further comprising storing at least some of the programs from the second list within a memory.

16. The method of claim 1, wherein presenting battery longevity information to a user comprises presenting the battery drain rates.

17. The method of claim 1, further comprising estimating battery longevities for each of the programs based on the battery drain rates for each of the programs, wherein presenting the battery longevity information to a user comprises presenting the battery longevities.

18. The method of claim 1, wherein presenting battery longevity information to a user comprises presenting an estimated length of battery service.

19. The method of claim 1, further comprising receiving selection of the parameters for each of the programs from the user.

20. A programming device comprising:

a telemetry circuit;

a user interface; and a processor to direct an implantable neurostimulator to deliver neurostimulation according to a plurality of programs during a programming session via the telemetry circuit, each of the programs including a plurality of parameters that define delivery of neurostimulation according to that program, estimate a battery drain rate for each of the programs based on the parameters for that program, and present battery longevity information to a user via the user interface based on the estimated battery drain rates.

21. The programming device of claim 20, wherein the parameters for each of the programs include at least one of a pulse amplitude, a pulse width, a pulse rate, and a duty cycle.

22. The programming device of claim 20, wherein the parameters for each of the programs include a number of anodes and a number of cathodes for delivery of neurostimulation according to that program, and the processor estimates a load for one of the programs based on the number of anodes and the number of cathodes for the program, and estimates the battery drain rate for the program based on the estimated load.

23. The programming device of claim 22, further comprising a memory to store an assumed per-electrode impedance, wherein the processor estimates the load based on the assumed per-electrode impedance.

24. The programming device of claim 20, wherein the processor receives device configuration information, estimates a load for one of the programs based on the device configuration information, and estimates a battery drain rate for the program based on the estimated load.

25. The programming device of claim 24, wherein the device configuration information includes at least one of an implantable neurostimulator type, a lead type, and electrode locations.

26. The programming device of claim 24, wherein the processor receives at least some of the device configuration information from the user via the user interface.

27. The programming device of claim 20, wherein the parameters for each of the programs include an identification of anodes and cathodes for delivery of neurostimulation according to that program, and the processor controls the implantable neurostimulator to measure the impedance for each of the anodes and cathodes identified by one of the programs, calculates a load for the program based on the measured impedances, and estimates the battery drain rate for the program based on the load.

28. The programming device of claim 20, wherein the processor presents the battery longevity information within a list of the programs.

29. The programming device of claim 28, wherein the processor orders the list according to the battery longevity information.

30. The programming device of claim 28, wherein the processor receives rating information for each of the programs, and presents the rating information within the list.

31. The programming device of claim 30, wherein the processor orders the list according to at least one of the battery longevity information and the rating information.

32. The programming device of claim 30, wherein rating information for each of the programs includes at least one of an efficacy score and an estimation of overlap of pain and paresthesia.

33. The programming device of claim 20, wherein the processor receives rating information for each of the programs, presents a first list of the tested programs that includes the rating information and is ordered according to the rating information, receives selections made by the user from the first list, presents a second list that includes the programs selected from the first list and the longevity information associated with the selected program, the second list ordered according to the longevity information, receives a selection made by the user of at least one program from the second list, and programs the implantable neurostimulator with the selected program via the telemetry circuit.

34. The programming device of claim 33, wherein the processor estimates drain rates for each of the programs selected from the first list upon selection.

35. The programming device of claim 33, further comprising a memory to store at least some of the programs from the second list.

36. The programming device of claim 20, wherein the battery longevity information comprises the estimated battery drain rates.

37. The programming device of claim 20, wherein the processor estimates battery longevities for each of the programs based on the battery drain rates for each of the programs, and the battery longevity information comprises the estimated battery longevities.

38. The programming device of claim 20, wherein processor presents an estimated length of battery service for each of the programs to the user via the user interface.

39. The programming device of claim 20, wherein the processor receives selection of the parameters for each of the programs from the user via the user interface.

40. A computer-readable medium comprising instructions that cause a programmable processor to:
   direct an implantable neurostimulator to deliver neurostimulation according to a plurality of programs during a programming session, each of the programs including a plurality of parameters that define delivery of neurostimulation according to that program;
   estimate a battery drain rate for each of the programs based on the parameters for that program; and
   present battery longevity information to a user based on the estimated battery drain rates.

41. The computer-readable medium of claim 40, wherein the parameters for each of the programs include at least one of a pulse amplitude, a pulse width, a pulse rate, and duty cycle.

42. The computer-readable medium of claim 40, wherein the parameters for each of the programs include a number of anodes and a number of cathodes for delivery of neurostimulation according to that program, and the instructions that cause a programmable processor to estimate a battery drain rate for one of the programs comprise instructions that cause a programmable processor to:
   estimate a load for the program based on the number of anodes and the number of cathodes; and
   estimate the battery drain rate based on the estimated load.

43. The computer-readable medium of claim 42, wherein the instructions that cause a programmable processor to estimate a load comprise instructions that cause a programmable processor to estimate the load based on an assumed per-electrode impedance.

44. The computer-readable medium of claim 40, further comprising instructions that cause a programmable processor to receive device configuration information, wherein the instructions that cause a programmable processor to estimate a battery drain rate for one of the programs comprise instructions that cause a programmable processor to:
   estimate a load based on the device configuration information; and
   estimate the battery drain rate for the program based on the estimated load.

45. The computer-readable medium of claim 44, wherein the device configuration information includes at least one of an implantable neurostimulator type, a lead type, and electrode locations.

46. The computer-readable medium of claim 40, wherein the parameters for each of the programs include an identification of anodes and cathodes for delivery of neurostimulation according to that program, and the instructions that cause a programmable processor to estimate a battery drain rate for one of the programs comprise instructions that cause a programmable processor to:
   control the implantable neurostimulator to measure the impedance for each of the anodes and cathodes identified by the program;
   estimate a load for the program based on the measured impedances; and
   estimates the battery drain rate for the program based on the estimated load.

47. The computer-readable medium of claim 40, wherein the instructions that cause a programmable processor to present battery longevity information comprise instructions that cause a programmable processor to present the battery longevity information within a list of the programs.

48. The computer-readable medium of claim 47, further comprising instructions that cause a programmable processor to order the list according to the battery longevity information.

49. The computer-readable medium of claim 47, further comprising instructions that cause a programmable processor to:
   receive rating information for each of the programs; and
   present the rating information within the list.

50. The computer-readable medium of claim 49, further comprising instructions that cause a programmable processor to order the list according to at least one of the battery longevity information and the rating information.

51. The computer-readable medium of claim 49, wherein the rating information for each of the programs includes at least one of an efficacy score and an estimation of overlap of pain and paresthesia.

52. The computer-readable medium of claim 40, further comprising instructions that cause a programmable processor to:
   receive rating information for each of the programs;
   present a first list of the tested programs, the first list ordered according to the rating information;
   receive selections made by the user from the first list;
   present a second list that includes the programs selected from the first list and the longevity information associated with the programs selected from the first list, the second list ordered according to the longevity information;
   receive selection of at least one program from the second list made by the user; and
   program the implantable neurostimulator with the selected program.

53. The computer-readable medium of claim 52, wherein the instructions that cause a programmable processor to estimate a battery drain rate for each of the programs comprise instructions that cause a programmable processor to estimate the drain rate for each of the programs selected from the first list upon selection from the first list.

54. The computer-readable medium of claim 52, further comprising instructions that cause a programmable processor to store at least some of the programs from the second list in a memory.

55. The computer-readable medium of claim 40, wherein the instructions that cause a programmable processor to display battery longevity information comprise instructions that cause a programmable processor to display the estimated drain rates.

56. The computer-readable medium of claim 40, further comprising instructions that cause a programmable processor to estimate battery longevities for each of the programs based on the battery drain rates for each of the programs, wherein the instructions that cause a programmable processor to present battery longevity information comprise instructions that cause a programmable processor to present the estimated battery longevities.

57. The computer-readable medium of claim 40, wherein the instructions that cause a programmable processor to present battery longevity information to a user comprise instructions that cause a programmable processor to present an estimated length of battery service for each of the programs.

58. The computer-readable medium of claim 40, further comprising instructions that cause a programmable processor to receive selection of the parameters for each of the programs from the user.

* * * * *